US007867756B2

(12) United States Patent
Hirao et al.

(10) Patent No.: US 7,867,756 B2
(45) Date of Patent: Jan. 11, 2011

(54) SPECIMEN ANALYZING IMPLEMENT

(75) Inventors: Konomu Hirao, Kyoto (JP); Yasuhito Murata, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 907 days.

(21) Appl. No.: 10/473,933

(22) PCT Filed: Apr. 11, 2002

(86) PCT No.: PCT/JP02/03591

§ 371 (c)(1),
(2), (4) Date: Oct. 3, 2003

(87) PCT Pub. No.: WO02/084291

PCT Pub. Date: Oct. 24, 2002

(65) Prior Publication Data

US 2004/0137640 A1 Jul. 15, 2004

(30) Foreign Application Priority Data

Apr. 12, 2001 (JP) ............................ 2001-114448

(51) Int. Cl.
*G01N 33/53* (2006.01)

(52) U.S. Cl. .................... 435/287.2; 436/514; 436/518; 436/524; 436/538; 436/535; 436/810; 436/807; 435/287.1; 435/287.8; 435/287.9

(58) Field of Classification Search ................. 436/514, 436/518, 524, 538, 535, 810, 807; 435/287.1, 435/287.2, 287.8, 287.9
See application file for complete search history.

(56) References Cited

U.S. PATENT DOCUMENTS 4,366,241 A * 12/1982 Tom et al. .................. 435/7.91
4,477,575 A 10/1984 Vogel et al.
4,774,192 A 9/1988 Terminiello et al.
5,087,556 A * 2/1992 Ertinghausen .............. 435/7.9
5,202,268 A * 4/1993 Kuhn et al. ................. 436/525
5,403,551 A 4/1995 Galloway et al.
5,500,375 A 3/1996 Lee-Own et al.
5,602,040 A 2/1997 May et al.
5,712,172 A * 1/1998 Huang et al. ................ 436/518
5,728,587 A * 3/1998 Kang et al. ................. 436/518
5,821,073 A 10/1998 Lee
5,824,268 A 10/1998 Bernstein et al.
5,846,837 A 12/1998 Thym et al.
6,040,195 A * 3/2000 Carroll et al. ............... 436/514
6,177,281 B1 1/2001 Manita (Continued)

FOREIGN PATENT DOCUMENTS

CA 2310762 6/1999

(Continued)

*Primary Examiner*—Bao-Thuy L Nguyen
(74) *Attorney, Agent, or Firm*—Hamre, Schumann, Mueller & Larson, P.C.

(57) ABSTRACT

A sample analysis device is provided in which a target component to be analyzed is prevented from being contaminated by a sample itself, which can be formed in an appropriate size, and which has excellent operability. In a sample analysis device 1 in which a sample is to be held in a porous sheet 13, supporting films 11 and 12 are stuck on front and rear faces of the porous sheet 13, respectively, and a sample supply hole 14 is formed in a part of the supporting films.

19 Claims, 10 Drawing Sheets

U.S. PATENT DOCUMENTS

| | | | | |
|---|---|---|---|---|
| 6,197,494 | B1 | 3/2001 | Oberhardt | |
| 6,287,867 | B1 | 9/2001 | Harttig et al. | |
| 6,475,805 | B1 * | 11/2002 | Charm et al. | 436/514 |

FOREIGN PATENT DOCUMENTS

| | | | |
|---|---|---|---|
| CN | 1215163 | | 4/1999 |
| DE | 19753850 | | 6/1999 |
| EP | 0 262 328 | | 4/1988 |
| EP | 0 299 428 | | 1/1989 |
| EP | 1 003 038 | | 5/2000 |
| EP | 1104886 | | 6/2001 |
| EP | 1114997 | | 7/2001 |
| JP | 63-96559 | | 4/1988 |
| JP | 64-32169 | | 2/1989 |
| JP | 5-5743 | | 1/1993 |
| JP | 6-341989 | | 12/1994 |
| JP | 7-72145 | | 3/1995 |
| JP | 8-54387 | | 2/1996 |
| JP | 8-503556 | | 4/1996 |
| JP | 96/35952 | | 11/1996 |
| JP | 8-511621 | | 12/1996 |
| JP | 9-178748 | | 7/1997 |
| JP | 10-10125 | | 1/1998 |
| JP | 10-132800 | | 5/1998 |
| JP | 10-332700 | | 12/1998 |
| JP | 11-44689 | | 2/1999 |
| JP | 11-505327 | | 5/1999 |
| JP | 2001-56339 | | 2/2001 |
| JP | 2001-66310 | | 3/2001 |
| WO | WO 88/08534 | * | 11/1988 |
| WO | WO 93/03673 | | 3/1993 |
| WO | 94/29696 | | 12/1994 |
| WO | 96/35952 | | 11/1996 |
| WO | WO 00/79279 | | 12/2000 |

* cited by examiner (A)

(B)

SPECIMEN ANALYZING IMPLEMENT

TECHNICAL FIELD

The present invention relates to a sample analysis device in which a porous sheet is used.

BACKGROUND ART

In the fields of clinical medicine and the like, sample analysis devices that are disposed of after being used once are used widely for fluid samples, for instance, body fluids such as blood, urine, and spinal fluid. In a sample analysis device composed of a porous sheet made of filter paper, a plastic film, etc., a sample such as blood is spotted on a part of the porous sheet, and it is spread through the inside of the porous sheet due to the capillary phenomenon. In the case where the sample is whole blood, blood cells are separated from blood plasma and blood serum due to the chromatography effect while the whole blood is being spread through the inside. The sample analysis device in which the sample is thus spread can be used, as it is, for holding the sample or for preserving the sample. Further, it is possible that, after a certain period of time elapses from the sampling of the sample, the porous sheet is removed out of the sample analysis device and a certain target component such as blood plasma, blood serum, etc. is extracted therefrom so that the extracted component is subjected to analysis. Further, in the case where an analytical reagent, etc. further is held in the porous sheet, the reagent and the component of the sample thus spread can be reacted with each other in the sample analysis device. Therefore, it is possible to observe the reaction directly in the sample analysis device by visual observation, and to analyze the reaction by an optical means or an electrochemical means.

In recent years, particularly, such sample analysis devices not only are used in hospitals, examination laboratories, etc., but also are applied in the remote diagnosis system whereby a patient him/herself collects a blood sample at home, and mails the collected sample held in the sample analysis device to a hospital so that tests are carried out on him/her without his/her going to the hospital. Further, a patient him/herself often carries out the sample analysis by using the sample analysis device through visual observation or by means of a simple measuring apparatus.

However, in such a case where the sample analysis device is handled by the patient him/herself who is not an expert, it is particularly important that the sample analysis device has excellent handlability. Therefore, for instance, a housed-type sample analysis device composed of a porous sheet as described above and a hollow plastic casing that houses the sheet therein is used widely at present, which is as disclosed in JP 7(1995)-46107 B.

DISCLOSURE OF THE INVENTION

However, in the case of such a housed-type sample analysis device, the production and assembly of the same require increased work and cost, since the structure of a housing container thereof is complex. Further, considering that it is disposed of after it is used once for a test and that a patient carries with him/her several devices necessary for tests, the further downsizing of the device is desired. However, in the case where such a housing container is used, it is difficult to further downsize the device.

The present invention was made in light of the above-described problems, and an object of the present invention is to provide a sample analysis device that is downsized further and that is produced easily at lower cost.

To achieve the foregoing object, the sample analysis device of the present invention is a sample analysis device having a porous sheet for holding a sample, which further includes a supporting film arranged on a front face of the porous sheet.

This sample analysis device of the present invention does not have a structure of being housed in a casing like the conventional housed-type sample analysis device, but has a structure in which a supporting film for supporting the porous sheet is arranged on a surface of the porous sheet. Such a very simple structure makes the production of the same easier, and enables the downsizing, thereby reducing the cost. Particularly, in the production process, it is possible to use a continuous manufacturing line using rolls or the like. Further, since the downsizing is enabled, it is possible to reduce a necessary amount of a sample. Still further, since the porous sheet is supported by the supporting film, the sample analysis device of the present invention has much flexibility and excellent operability.

It should be noted that, as will be described later, the sample analysis device of the present invention can be used, for instance, as a device for holding a sample so that the sample is mailed, and also, as an analyzing device for analyzing a target component.

Examples of the sample analysis device of the present invention include the following two types.

A first sample analysis device is configured so that the supporting film is stuck on a front face of the porous sheet, and a sample supply hole is formed in a part of the supporting film.

The sample analysis device of this configuration achieves the downsizing and the reduction of cost as described above, as well as the following effects described below also.

In the conventional housed-type sample analysis device as described above, sometimes a fluid sample infiltrates not into the inside of the porous sheet but between the porous sheet and an interior wall of the container. Then, in the case where, for instance, it is necessary to separate blood plasma and blood serum from blood cells as in the case of a whole blood sample, the fluid sample having infiltrated between the porous sheet and the interior wall of the container, which has not been subjected to the separation due to the chromatography effect, could contaminate the component separated in the porous sheet, thereby adversely affecting the analysis. As a means for solving this problem, the sample spreading part of the porous sheet may be increased sufficiently. However, this excessively increases the size of the sample analysis device, makes operations difficult and causes inconveniences, as well as causes disadvantages in terms of cost.

Thus, in the conventional sample analysis device, the infiltration of a sample between the interior wall of the container and the porous sheet is caused by the capillary phenomenon. However, even if the porous sheet and the interior wall of the container are brought into close contact in a conventional sample analysis device, it is difficult to prevent the capillary phenomenon effectively. Therefore, in the first sample analysis device of the present invention, the supporting of the porous sheet is achieved not by containing the porous sheet into a container but sticking the supporting film on the front face of the porous sheet. This prevents the capillary phenomenon from occurring between the porous sheet and the interior wall of the container, thereby preventing the contamination by non-separated sample, and also enabling the downsizing as described above. Further, by being supported by a supporting film, the sample analysis device of the present invention has much flexibility and excellent operability. It should be noted that the "front face" of the porous sheet is a face on a side on which a sample is supplied, while the "rear face" is a face opposite to the front face.

In the first sample analysis device of the present invention, it is preferable that a supporting film is stuck not only on the front face of the porous sheet, but another supporting film is stuck also on a rear face of the porous sheet. This is because in the case where supporting films are stuck on both faces of the porous sheet, respectively, effects as described below can be achieved further.

The sample analysis device employing such a porous sheet, with an analytical reagent impregnated in the porous sheet, is capable of spreading a sample in the porous sheet while causing a target component in the sample and the analytical reagent to react with each other, so as to detect the target component in the sample. In the case of such a sample analysis device impregnated with a reagent, particularly in the case where several types of reagents (labeled antibodies, label-detection reagents, etc.) are arranged at several positions in a sample spreading direction in the porous sheet and a sample is caused to react with each reagent stepwise, it is desired that times while samples are spread (sample spreading times) are uniform among a plurality of sample analysis devices. In other words, if the sample spreading times are different, the times of reaction with a reagent are also different among the sample analysis devices, and this adversely affects the measurement results. Studying the causes of such variation of the spreading time, the inventors consequently found that the measurement results tend to be influenced by environmental conditions such as temperature and humidity, and the influence of humidity is particularly significant. For instance, in the case where humidity is relatively low, the spreading time is prolonged due to evaporation of the sample. Then, by sticking supporting films on both sides of the porous sheet as described above, the inventors were successful in suppressing the evaporation of moisture from the porous sheet, and by so doing, making sample spreading times of sample analysis devices uniform. With the uniform spreading times, the times of reaction with a reagent also are made uniform, and this further improves the measurement reproducibility.

In the first sample analysis device of the present invention, it is preferable that a part of a side face of the porous sheet is exposed to outside. Further, it is also preferably that air vent holes are formed in a part of the supporting film. This configuration causes the capillary phenomenon to occur intensely in the porous sheet.

The first sample analysis device preferably further includes a protective film that is to be stuck on a surface of the supporting film having the sample supply hole after the sample is supplied. This is because this configuration prevents the alteration of the sample when the sample is held or preserved.

In the first sample analysis device of the present invention, the porous sheet preferably is an asymmetric porous sheet in which the diameters of pores vary in a thickness direction of the sheet, more preferably an asymmetric porous sheet that further has a groove that is formed parallel with a width direction of the sheet. In the asymmetric porous sheet, the variation of the pore diameter may be continuous or stepwise.

Next, a second sample analysis device of the present invention is characterized in that a through hole is formed in a part of the supporting film so as to constitute a sample supply hole, the supporting film functions as a cover film, and the porous sheet is caught directly or indirectly by the cover film and a base film so that the porous sheet, the cover film, and the base film are integrally provided. It should be noted that in the second sample analysis device, the supporting film arranged on the front face of the porous sheet is referred to as "cover film", while a film arranged on the rear face of the porous sheet is referred to as "base film".

The second sample analysis device does not have a configuration of being housed in a casing but has a configuration in which the three members are integrally provided, unlike the conventional housed-type sample analysis device, as described above. Therefore, this simplifies the structure, thereby making the production of the same easier, and enabling the downsizing, whereby the cost is reduced. Further, in the case where a test is carried out using this sample supply device with a reagent being held therein, the downsizing is enabled, and therefore, it is possible to reduce a necessary amount of a sample. It should be noted that in the present invention, "the porous sheet is caught directly" means that the porous sheet is caught directly by the cover film and the base film, and "the porous sheet is caught indirectly" means that, for instance, the porous sheet is caught by the cover film and the base film with other members being interposed therebetween.

Examples of embodiments of the second sample analysis device of the present invention include the following two types.

As one embodiment of the same, it is preferable that the porous sheet is arranged on the base film, and the base film and the cover film are bonded with each other at ends thereof in a lengthwise direction using a bonding member.

As another embodiment of the same, it is preferable that a pair of the base films are provided, which partially are bonded with ends of the cover film in a lengthwise direction thereof via bonding members, respectively, and each of which has a protrusion that protrudes toward the center in the lengthwise direction from the bonding member, and ends of the porous sheet in the lengthwise direction are arranged on the projections, respectively.

In the second sample analysis device of the present invention, the porous sheet preferably has a lining layer on its bottom face. In the case where the porous sheet has the lining layer, for instance, the strength is increased further, and the handlability also is improved. Particularly even if the base film is not arranged over an entirety of the bottom face of the porous sheet as in the latter embodiment described above, the strength can be maintained, which is preferable.

The second sample analysis device of the present invention preferably further includes a separating layer for separating and removing unnecessary matters in the sample. The separating layer is arranged between the cover film and the porous sheet at a position corresponding to the sample supply hole. With the separating layer thus provided, even in the case where, for instance, a component of blood plasma or blood serum in whole blood is to be analyzed, the analysis can be carried out easily by directly using whole blood, without conducting an independent process of removing blood cells.

Further, likewise, the second sample analysis device of the present invention further includes a sample holding layer for temporarily holding the sample, arranged at a position corresponding to the sample supply hole. With the sample holding layer thus provided, it is possible, for instance, to supply the sample held in the sample holding layer gradually to the porous sheet. Further, the second sample analysis device may include both of the separating layer and the sample holding layer. In this case, it is preferable that the sample holding layer is arranged on the porous sheet with the separating layer being interposed therebetween.

In the second sample analysis device of the present invention, the cover film preferably further includes a through hole that constitutes a spreading solvent supply hole on an upstream side with respect to the sample supply hole in a direction in which the sample is spread in the porous sheet. Further, the second sample analysis device preferably further includes a spreading solvent holding layer for holding a spreading solvent and supplying the same to the porous sheet. The spreading solvent holding layer is arranged between the cover film and the porous sheet at a position corresponding to the spreading solvent supply hole. With the spreading solvent holding layer thus provided, the spreading solvent infiltrates from the spreading solvent holding layer into the porous sheet and is diffused therein. Therefore, the spreading of the sample thus diffused in the porous sheet is aided and promoted. It should be noted that the direction in which the sample is spread in the porous sheet varies depending on, for instance, the type of the porous sheet-used, but the sample spreading direction in the present invention is a lengthwise direction of the sample analysis device, and the direction in which most of the sample is spread is a downstream side.

The second sample analysis device of the present invention preferably further includes an absorbing layer (water-absorbing layer) arranged between the cover film and the porous sheet at an end on a downstream side in a direction in which the sample is spread in the porous sheet. With the absorbing layer thus provided, for instance, a sample solution reaching a position where the porous sheet is in contact with the absorbing layer is absorbed by the absorbing layer. Therefore, the sample being spread becomes in a drawn state, whereby the spreading of the sample is promoted.

In the second sample analysis device of the present invention, the separating layer, the spreading solvent holding layer, and the absorbing layer preferably are bonded with the cover film using a bonding member.

In the second sample analysis device of the present invention, at least one of the cover film and the base film preferably has a detection part on a downstream side with respect to the sample supply hole in a direction in which the sample is spread in the porous sheet.

The detection part may be a through hole formed in at least one of the cover film and the base film, or in the case where a through hole is not provided, the detection part in the at least one of the cover film and the base film preferably is optically transparent. Thus, in the case where the detection part is optically transparent, there is no need to provide a through hole, and in the case where the entirety of the cover film or the base film is optically transparent, the detection is allowed at any position.

In the second sample analysis device of the present invention, the porous sheet preferably has a reagent part containing a reagent on a downstream side with respect to the sample supply hole in a direction in which the sample is spread in the porous sheet, or has a reagent part between the sample supply hole and the detection part.

In the second sample analysis device of the present invention, at least a part of the lining layer corresponding to the detection part preferably is optically transparent. If the lining layer is optically transparent, the detection is enabled from the rear side of the porous sheet.

In the second sample analysis device of the present invention, the bonding member preferably is a double-faced tape, since it is easy to handle.

In the first and second sample analysis device of the present invention as described above, the porous sheet preferably has a sample-spotted part at which the sample is to be spotted, and one or more reagent parts containing one or more reagents, and the reagent parts are arranged around the sample-spotted part so that when the sample is spotted on the sample-spotted part, the sample is spread radially and reaches the reagent parts. In such a sample analysis device, for instance, in the case where a plurality of reagent parts containing different reagents are arranged, it is possible to analyze a sample regarding a plurality of items at the same time, since the sample is spread radially only by spotting the sample at the sample-spotted part.

Further, a sample for the sample analysis device of the present invention is a sample that can be transferred (spread) through the inside of the porous sheet due to the capillary phenomenon, and it is not limited to a fluid sample, and may be a sol-state sample, for example. Even in the case of a solid-state sample, by dissolving the sample in a buffer or the like so that it is transferred through the inside of the porous sheet due to the capillary phenomenon, the sample can be analyzed by the sample analysis device of the present invention. Examples of samples applicable in the sample analysis device of the present invention include whole blood, blood plasma, blood serum, urine, spinal fluid, saliva, and secreta.

BRIEF DESCRIPTION OF DRAWINGS

FIG. 1A is a plan view of the device. FIG. 1B is a cross-sectional view of the device along an arrow line I-I, viewed in a direction indicated by the arrows. FIG. 1C is a perspective view of the device.

FIG. 2A is a plan view of the device. FIG. 2B is a cross-sectional view of the device along an arrow line II-II, viewed in a direction indicated by the arrows.

FIG. 3A is a plan view of the device. FIG. 3B is a cross-sectional view of the device along an arrow line III-III, viewed in a direction indicated by the arrows. FIG. 3C is a cross-sectional view of the device along an arrow line IV-IV, viewed in a direction indicated by the arrows.

FIG. 5A is a perspective view of the sheet. FIG. 5B is a cross-sectional view of the sheet along an arrow line V-V, the sheet being viewed in a direction indicated by the arrows.

FIG. 6A is a plan view of the device. FIG. 6B is a cross-sectional view of the device along an arrow line VI-VI shown in the foregoing plan view, viewed in a direction indicated by the arrows. FIG. 6C is a bottom view of the device.

FIG. 7A is a plan view of the device. FIG. 7B is a cross-sectional view of the device along an arrow line VII-VII shown in the foregoing plan view, viewed in a direction indicated by the arrows. FIG. 7C is a bottom view of the device.

DESCRIPTION OF THE INVENTION

The porous sheet used in the sample analysis device of the present invention is not limited particularly as long as, for instance, a fluid as described above is spread therein due to the capillary phenomenon. Examples of the same include filter paper, sheets made of cellulose derivatives, porous sheets made of resins, glass filters, sheets made of gels, and sheets made of silica fibers. Examples of the sheets made of cellulose derivatives include a cellulose film, a cellulose acetate film, and a nitrocellulose film. Examples of the porous sheets made of resins include sheets made of polyester, polysulfone, polycarbonate, cellulose acetate, fluorocarbon resin, polytetrafluoroethylene (PTFE), and other materials. These sheets may be used alone or in combination of two or more types. Preferable porous sheets among these are filter paper, porous sheets made of nitrocellulose, porous sheets made of polysulfone, and porous sheets made of polyester, and porous sheets made of polycarbonate, and more preferable ones are filter paper, sheets made of nitrocellulose, porous sheets made of polysulfone, and porous sheets made of polyester. An average diameter of pores of the porous sheet is, for instance, 1 μm to 500 μm, preferably 2 μm to 100 μm, more preferably 5 μm to 50 μm.

Further, the porous sheet may be impregnated with an analytical reagent. The type of the reagent is not limited particularly, and may be determined appropriately according to, for instance, the type of a target component in the analysis. Examples of the reagent include various types of enzymes, buffers such as phosphates and carbonates, couplers, antigens, and antibodies. More specifically, in the case where the target component in the analysis is glucose, it is possible to use, for instance, a combination of glucose oxidase (GOD) and 4-aminoantipyrine, glucokinase, glucose-6-phosphate dehydrogenase, β-nicotinamide adenine dinucleotide phosphate (β-NADP), and adenosine triphosphate (ATP). Further, in the case where the target component in the analysis is albumin (Alb), it is possible to use, for instance, bromcresol green (BCG). In the case where the target component in the analysis is total bilirubin (T-Bil), it is possible to use, for instance, sulfanilic acid or nitrous acid.

Figure 9A:
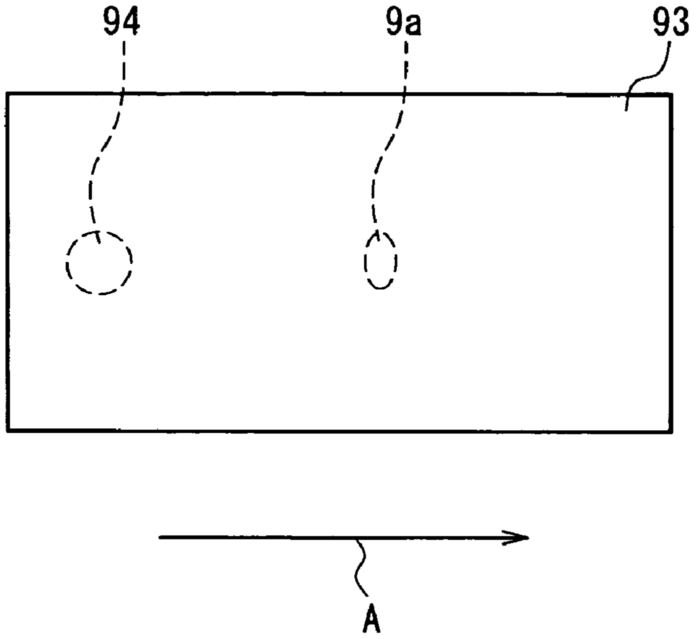
FIG. 9A is a plan view illustrating an example of a porous sheet used in a sample analysis device of the present invention.
Figure 9B:
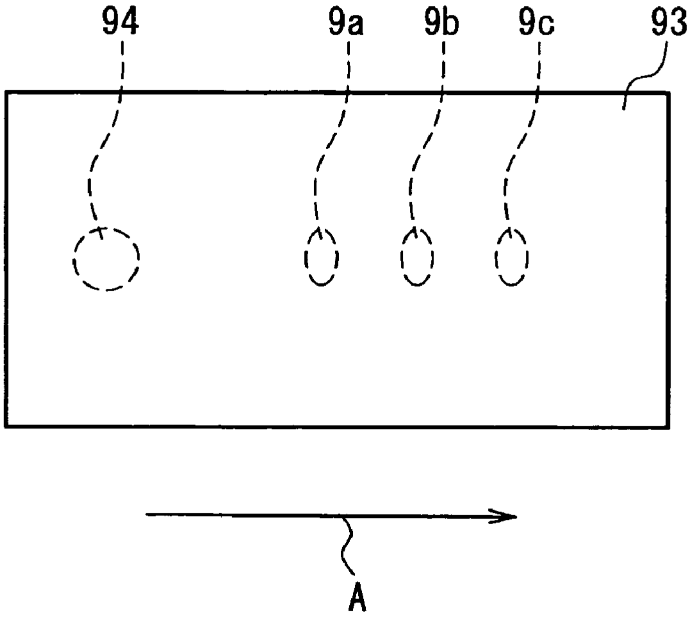
FIG. 9B is a plan view illustrating another example of a porous sheet.
Figure 10:
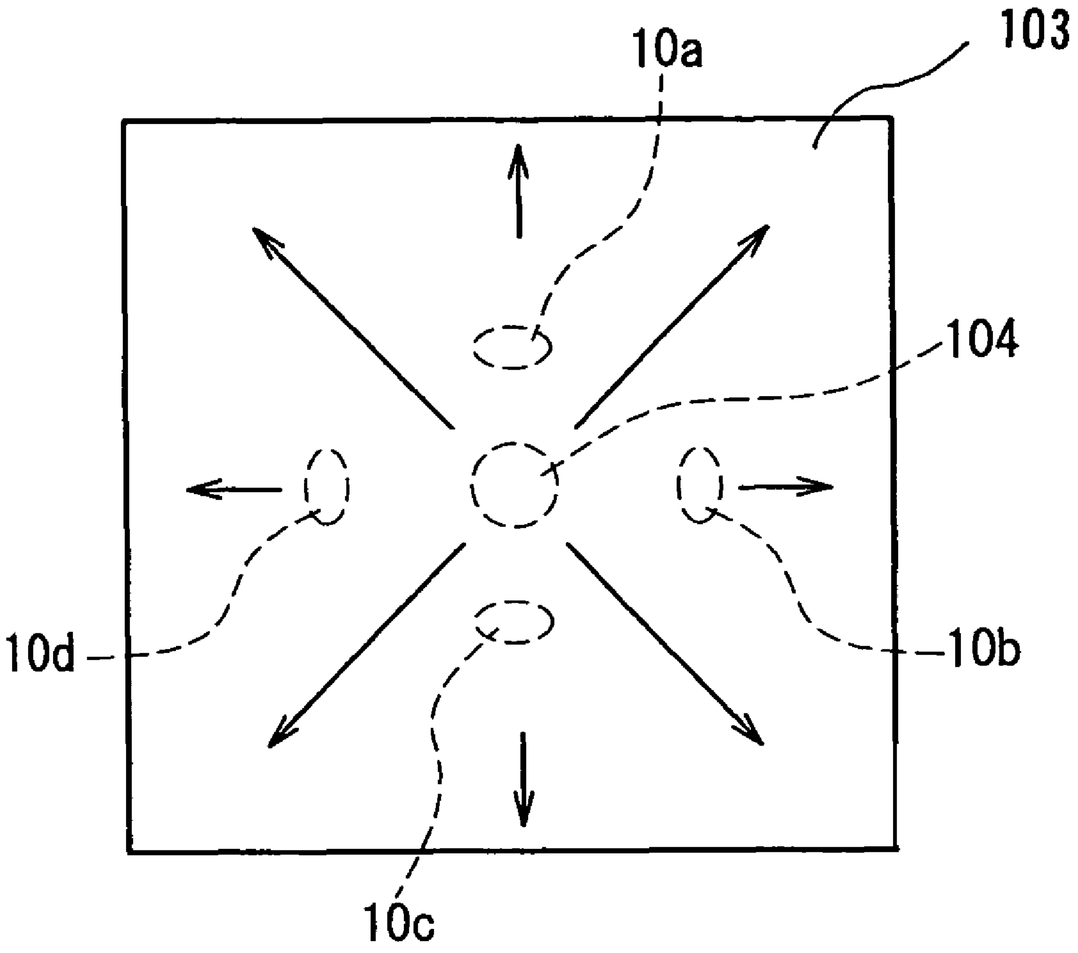
FIG. 10 is a plan view illustrating still another example of a porous sheet used in a sample analysis device of the present invention.

In the case where the porous sheet is impregnated with an analytical reagent, the position for the impregnation can be determined appropriately according to the type of the analysis target, the type of the sample, etc. For instance, in the case where a sample is spread in one direction, as shown in FIG. 9A, a reagent 9*a* may be arranged on a downstream side with respect to a sample-spotted portion 94 of the porous sheet 93 in a direction in which a sample is spread (a direction indicated by an arrow A in the drawing). Further, the number of positions where the reagent is spotted is not limited to one, and in the case where the target components of the sample is reacted with a plurality of reagents successively as in immunochromatography, for instance, reagents (9*a*, 9*b*, and 9*c*) may be arranged as shown in FIG. 9B at a plurality of positions toward the downstream side in the sample spreading direction (a direction indicated by an arrow A in the drawing). In the case where the sample is spread radially, as shown in FIG. 10, reagents (10*a*, 10*b*, 10*c*, 10*d*) may be arranged radially (indicated by arrows in the drawing) with respect to a sample-spotted portion 104 of the porous sheet 103 as a center. In the case where reagents are different from one another, the foregoing configuration allows a plurality of target components to be detected by spotting the sample at only one position.

Further, a material for preventing components in the sample from alteration may be held in the porous sheet. Examples of such an alteration inhibitor include saccharose, trehalose, and adonitol.

Figure 5:
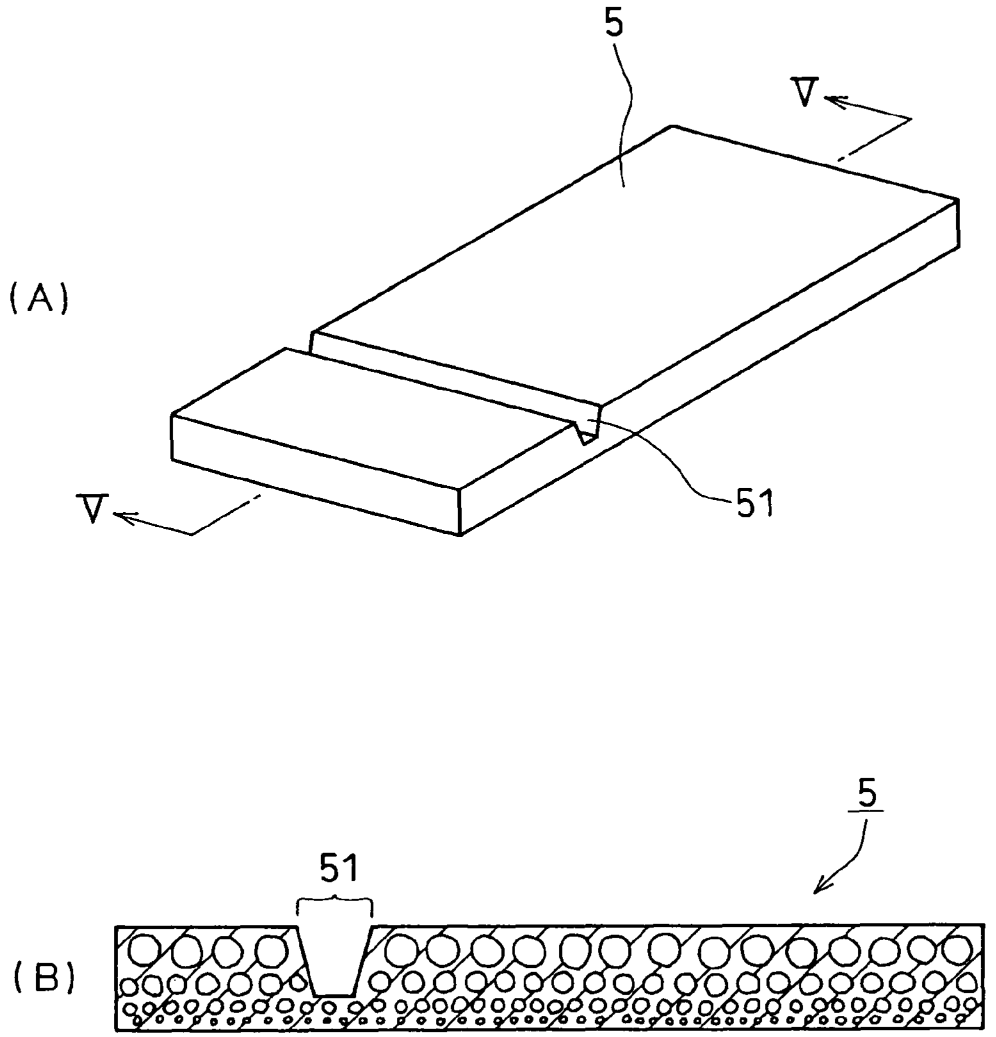
FIGS. 5A and 5B are views illustrating an example of a configuration of an asymmetrical porous sheet.

The porous sheet may be, for instance, an asymmetric porous sheet in which the diameters of the pores vary continuously or stepwise in either a thickness direction or a planar direction of the sheet, preferably an asymmetric porous sheet in which the diameters of the pores vary in a thickness direction of the sheet. More preferably, it is an asymmetric porous sheet that further has a groove that is formed parallel with a width direction of the sheet. An example of the sheet having the groove is shown in FIGS. 5A and 5B. FIG. 5A is a perspective view of an asymmetric porous sheet 5, and FIG. 5B is a cross-sectional view of the same taken along a line V-V in the perspective view. As shown in the drawings, in the single layer porous sheet 5, the pore diameter continuously decreases from the upper side to the lower side in the thickness direction of the sheet, and a groove 51 is formed therein that is parallel with the width direction of the sheet. When whole blood, for instance, is spotted on this sheet, blood cells are separated from blood plasma and blood serum due to the chromatography effect while the whole blood is being transferred in the sheet. Here, blood cells are separated from blood plasma and blood serum due to the sieving effect when the whole blood is transferred in the sheet thickness direction, and the separation of the blood cells is further ensured by the groove 51. The width of the groove is not limited particularly, and it is, for instance, 0.2 mm to 5 mm, preferably 0.5 mm to 3 mm, more preferably 1 mm to 1.5 mm. The depth of the groove is determined appropriately according to the thickness of the sheet, the distribution of the pore diameter in the sheet, and the like. For instance, when the thickness of the sheet is in a range of 10 μm to 2000 μm, the depth of the groove is, for instance, 5 μm to 1000 μm, preferably 5 μm to 500 μm, more preferably 200 μm to 300 μm. Further, an average diameter of the pores in a portion from the bottom face of the sheet to the bottom face of the groove preferably is such that the blood cells do not pass through the pores.

The type of the supporting film for use in the sample analysis device of the present invention is not limited particularly, and a film made of resin can be used as the same, for instance. Examples of the film made of resin include films made of nylon, polyester, cellulose acetate, polyethylene (PE), polyethylene terephthalate (PET), acrylic resin, polyvinyl chloride (PVC), polypropylene (PP), acrylonitrile-butadiene-styrene copolymer (ABS resin), epoxy resin, and other materials. Among these, PP, ABS resin, and PVC are preferable, and PVC and ABS resin are more preferable. Apart from these, synthetic rubbers can be used.

The size of the supporting film is determined appropriately according to the size of the porous sheet. The supporting film preferably has a tensile strength of, for instance, not less than 700 $kg/cm^2$, more preferably in a range of 750 $kg/cm^2$ to 800 $kg/cm^2$.

Embodiment A

The following will describe the first sample analysis device of the present invention. It should be noted that the present invention is not limited to these embodiments. In the first sample analysis device, the porous sheet has an average thickness of, for instance, 10 μm to 2000 μm, preferably 100 μm to 1000 μm, more preferably 300 μm to 500 μm. The size thereof is determined appropriately according to the purpose of use of the same (the kind of the test, etc.) and the like. In the case where it is in a rectangular shape (rectangular or square shape), it has a size of, for example, 20 mm×20 mm to 2 mm×250 mm, preferably 20 mm×25 mm to 3 mm×150 mm, more preferably 20 mm×30 mm to 25 mm×40 mm. On the other hand, the size of the supporting film is determined appropriately according to, for instance, the size of the foregoing porous sheet, and the thickness of the supporting film is in a range of, for instance, 20 μm to 500 μm, preferably in a range of 50 μm to 300 μm, more preferably in a range of 100 μm to 200 μm.

The first sample analysis device of the present invention can be produced by sticking the supporting films on the porous sheet. The sticking can be achieved by using, for instance, an adhesive, a double-faced tape, etc. The adhesive preferably does not flow into pores of the porous sheet, and is insoluble in an extraction solution used for the extraction process with respect to a sample. A rubber-based adhesive, for instance, is usable as the foregoing adhesive. Specific examples of the rubber-based adhesive include butanol-based adhesives and epoxy-based adhesives.

To prevent a non-separated sample from infiltrating into gaps between the porous sheet and the supporting films (the capillary phenomenon), the supporting films preferably are stuck over an entirety of a surface of the porous sheet. However, in some cases, the supporting films may be applied on the porous sheet so that a part of the same is stuck on a certain range of the porous sheet at a position where the sample is to be supplied, while the other part of the same is in contact with the porous sheet. In this case, an adhesive or the like may be applied on the range thereof at the stuck position. For instance, in the case where an asymmetric porous sheet having a groove thereon that is parallel with a sheet width direction is used, the supporting films may be stuck in a range from the sample supply position over the groove.

Embodiment A-1

Figure 1:
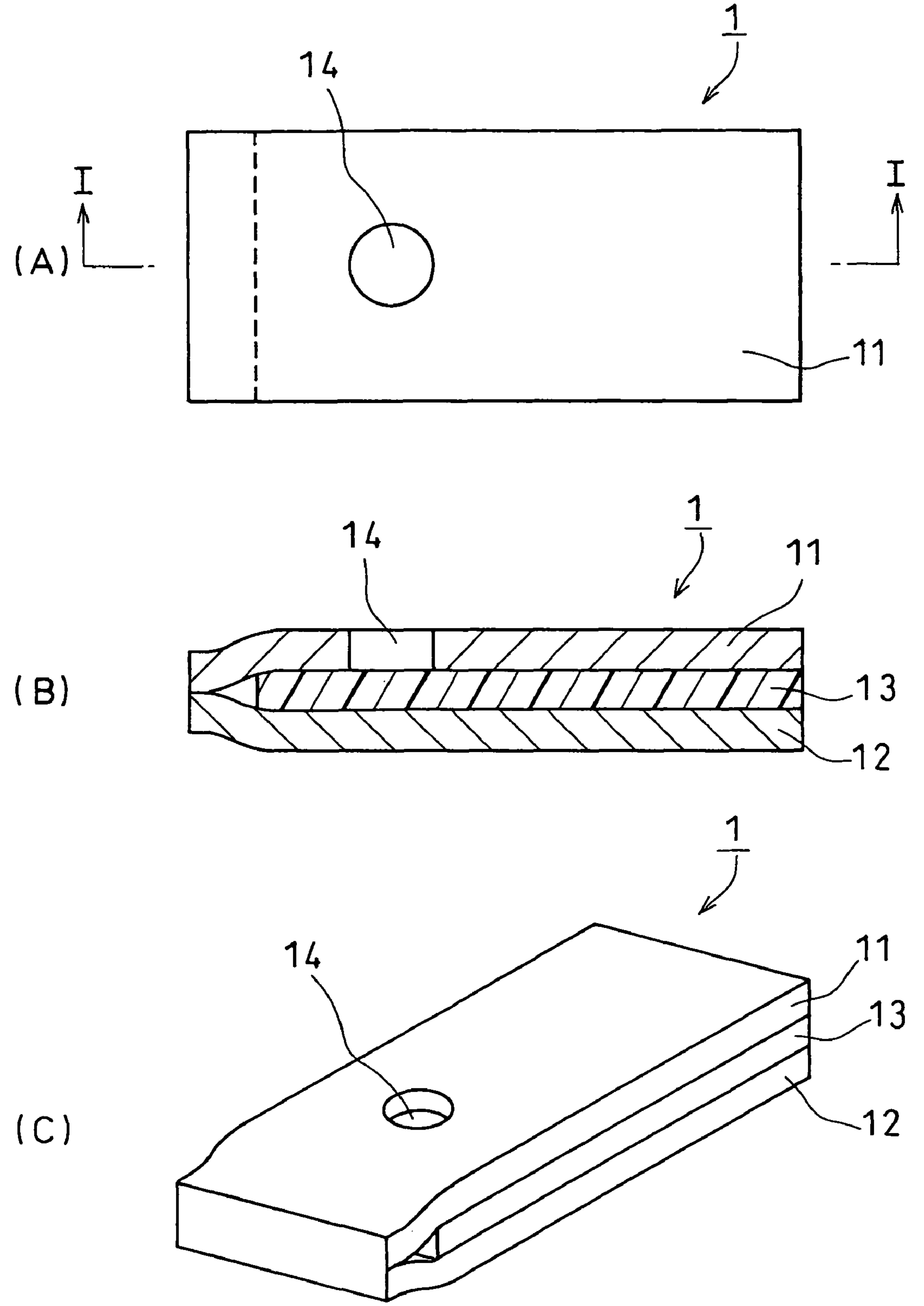
FIGS. 1A to 1C are views illustrating an example of a sample analysis device of the present invention.

A first example of the first sample analysis device is shown in FIGS. 1A to 1C. FIG. 1A is a plan view schematically illustrating the sample analysis device. FIG. 1B is a cross-sectional view of the device along an arrow line I-I, viewed in a direction indicated by the arrows. FIG. 1C is a perspective view of the device. It should be noted that FIGS. 1A to 1C illustrate the sample analysis device partially with exaggeration for making the configuration of the device understood easily, and therefore the drawings are different from an actual sample analysis device in some cases. This also applies to FIGS. 2A and 2B, FIGS. 3A to 3C, and FIG. 4 described below.

As shown in FIGS. 1A to 1C, the sample analysis device 1 is formed by sticking supporting films 11 and 12 on front and rear faces of a single layer porous sheet 13, respectively. A sample supply hole 14 is fanned at a predetermined position in the supporting film 11, which is stuck on the front face. Further a side face of an end portion in a lengthwise direction of the porous sheet 13 is sealed by sticking ends of the supporting films 11 and 12 with each other, while the other side faces of the porous sheet 13 are exposed to the outside. In the case where thus all or part of the side faces of the porous sheet 13 are exposed to the outside, the capillary phenomenon in the porous sheet is caused intensely.

Regarding size, the sample analysis device 1 has, for instance, an overall length of 20 mm to 250 mm, a width of 2 mm to 50 mm, a maximum thickness of 50 μm to 3000 μm, and a diameter of the sample supply hole 14 of 1 mm to 20 mm; preferably it has an overall length of 25 mm to 150 mm, a width of 20 mm to 30 mm, a maximum thickness of 150 μm to 1500 μm, and a diameter of the sample supply hole 14 of 5 mm to 15 mm; more preferably it has an overall length of 30 mm to 40 mm, a width of 20 mm to 25 mm, a maximum thickness of 500 μm to 1000 μm, and a diameter of the sample supply hole 14 of 8 mm to 12 mm.

The following will describe an example of a sample analysis employing the foregoing sample analysis device, referring to a case where whole blood is used as a sample. First, the whole blood is dripped through the sample supply hole 14 so that the whole blood adheres to the porous sheet 13. The whole blood is transferred through the inside of the porous sheet 13 due to the capillary phenomenon, and is separated into blood cells and blood plasma (blood serum) due to the chromatography effect while it is being transferred in a sheet length direction. Here, the whole blood does not infiltrate between the porous sheet 13 and the supporting films 11 and 12. In the case where a detection reagent or the like is arranged in the porous sheet, the reagent and components in the sample react with each other, which is measured by an optical means such as a spectrophotometer or a reflectometer, or by an electrochemical means using a sensor or the like. Further, in the case where a detection reagent or the like is not held, the sample analysis device is cut finely and put into an extraction solution such as a buffer solution so that components in the sample are extracted and analyzed. The extraction of the components of the sample preferably is carried out after the supporting films are removed, though the extraction may be carried out without removing the supporting films.

It should be noted that by sticking the supporting films on both faces of the porous sheet, the time while a sample is spread (spreading time) in the porous sheet is made constant.

Embodiment A-2

Figure 2:
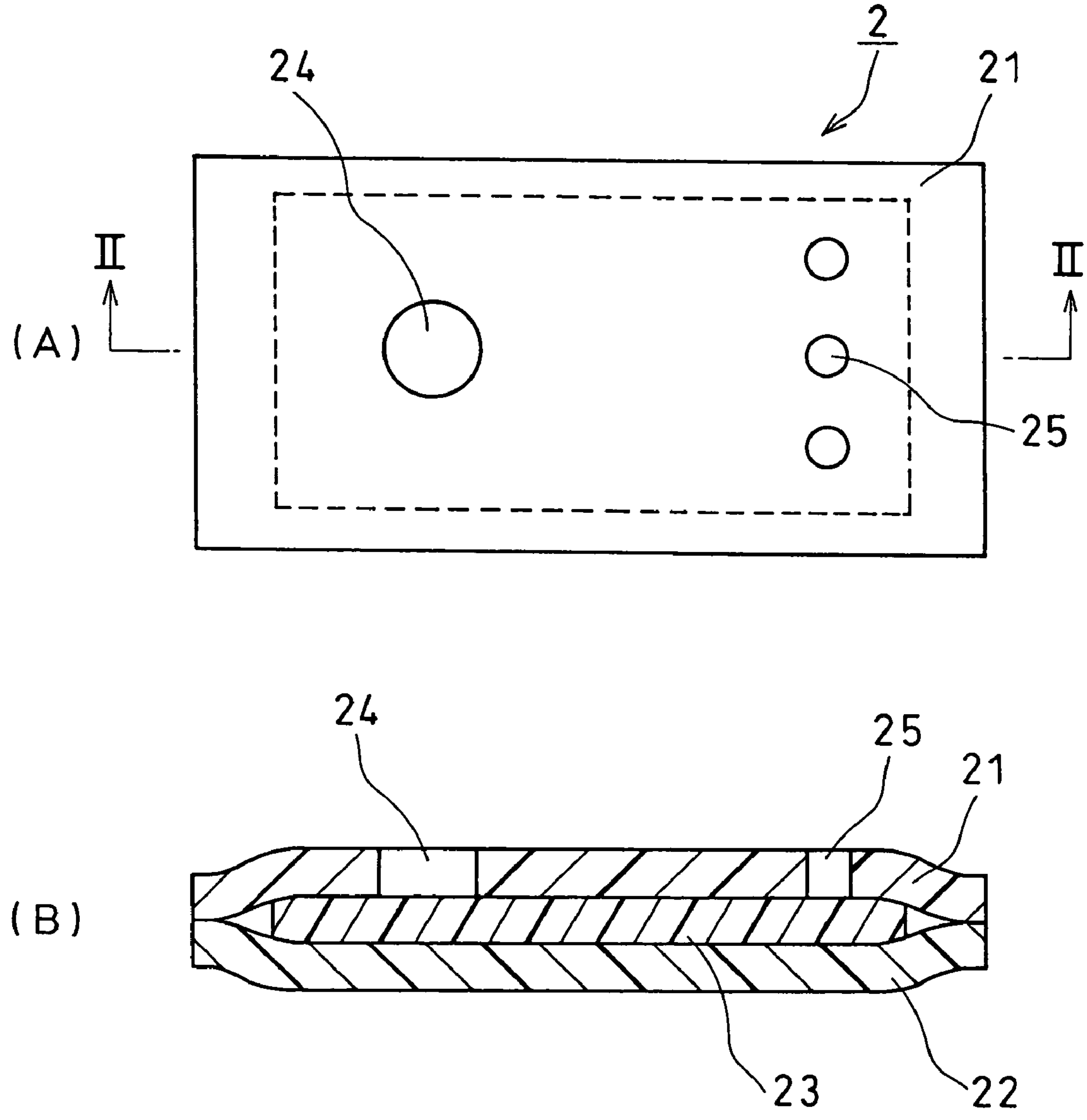
FIGS. 2A and 2B are views illustrating another example of a sample analysis device of the present invention.

A second example of the first sample analysis devices is shown in FIGS. 2A and 2B. FIG 2A is a plan view schematically illustrating the sample analysis device. FIG. 2B is a cross-sectional view of the device along an arrow line II-II, viewed in a direction indicated by the arrows. This sample analysis device is, like the first example described above, formed by sticking supporting films 21 and 22 on front and rear faces of a single layer, porous sheet 23. It should be noted that in the present sample analysis device, peripheral portions of the two supporting films 21 and 22 are bonded with each other so that all of the side faces of the porous sheet 23 are sealed. Further, three air vent holes 25 are formed together with a sample supply hole 24 in the supporting film 21 on the front face so that the capillary phenomenon in the porous sheet 23 is intensified. The air vent hole 25 is a hole formed through only the supporting film 21 on the front face, but it may be formed through the porous sheet 23 and the supporting film 22 on the rear face as well.

Regarding size, the sample analysis device 2 has, for instance, an overall length of 21 mm to 270 mm, a width of 3 mm to 70 mm, a maximum thickness of 50 μm to 3000 μm, a diameter of the sample supply hole 24 of 1 mm to 20 mm, and a diameter of the air vent hole 25 of 1 mm to 20 mm; preferably it has an overall length of 27 mm to 160 mm, a width of 22 mm to 40 mm, a maximum thickness of 150 μm to 1500 μm, a diameter of the sample supply hole 24 of 5 mm to 15 mm, and a diameter of the air vent hole 25 of 2 mm to 10 mm; more preferably it has an overall length of 33 mm to 44 mm, a width of 23 mm to 29 mm, a maximum thickness of 500 μm to 1000 μm, a diameter of the sample supply hole 24 of 8 mm to 12 mm, and a diameter of the air vent hole 25 of 3 mm to 5 mm. Except for these differences, the sample analysis device 2 is identical to the sample analysis device 1 of the first example described above, and operations of the same also are identical.

Embodiment A-3

Figure 3:
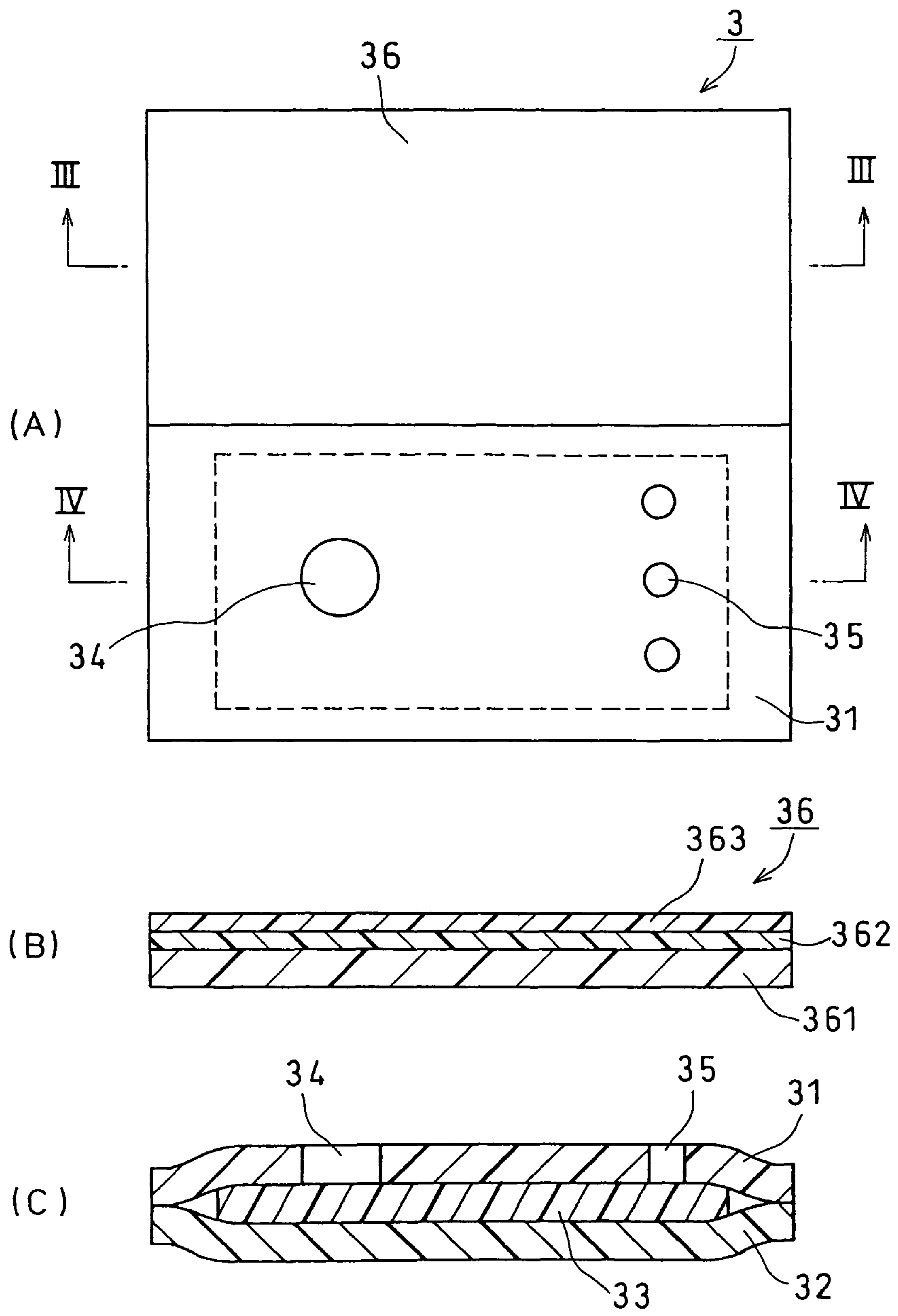
FIGS. 3A to 3C are views illustrating still another example of a sample analysis device of the present invention.

A third example of the first sample analysis device is shown in FIGS. 3A to 3C. FIG. 3A is a plan view schematically illustrating the sample analysis device. FIG. 3B is a cross-sectional view of the device along an arrow line III-III, viewed in a direction indicated by the arrows. FIG. 3C is a cross-sectional view of the device along an arrow line IV-IV, viewed in a direction indicated by the arrows. As shown in the drawings, the sample analysis device 3 of this example has a configuration identical to the sample analysis device of the second example described above, except that the sample analysis device 3 further includes a protective film 36. More specifically, supporting films 31 and 32 are stuck over front and rear faces of a single layer porous sheet 33, respectively, and peripheral portions of the two supporting films 31 and 32 are bonded with each other so that all of side faces of the porous sheet 33 are sealed. A sample supply hole 34 and three air vent holes 35 are formed in the supporting film 31 on the front face. The supporting film 32 on the rear face is provided integrally with a film body 361 of the protective film 36. The protective film 36 is configured in the following manner. A bonding layer 362 is formed on the film body 361, and a separating sheet (liner) 363 is arranged further on the bonding layer 362. Except for these configurations, the sample analysis device 3 is identical to the second example described above.

Examples of a material for the film body 361 of the protective film 36 include polyethylene, polyvinyl chloride, polypropylene, ABS resin, and epoxy resin. The film body 361 preferably is made of either polypropylene, ABS resin, or polyvinyl chloride, more preferably, either polyvinyl chloride or ABS resin. The protective film 36 has a thickness of, for instance, 20 μm to 500 μm, preferably 50 μm to 300 μm, more preferably 100 μm to 150 μm. Further, the size of the protective film preferably is set so that the protective film covers a surface of the supporting film 31 on the front face as will be described later, and normally it is set to be equal to the size of the supporting film 31 on the front face. As an adhesive for the bonding layer 362, the same adhesive as that described above can be used. As the separating sheet 363, a generally used separating sheet can be used.

Figure 4:
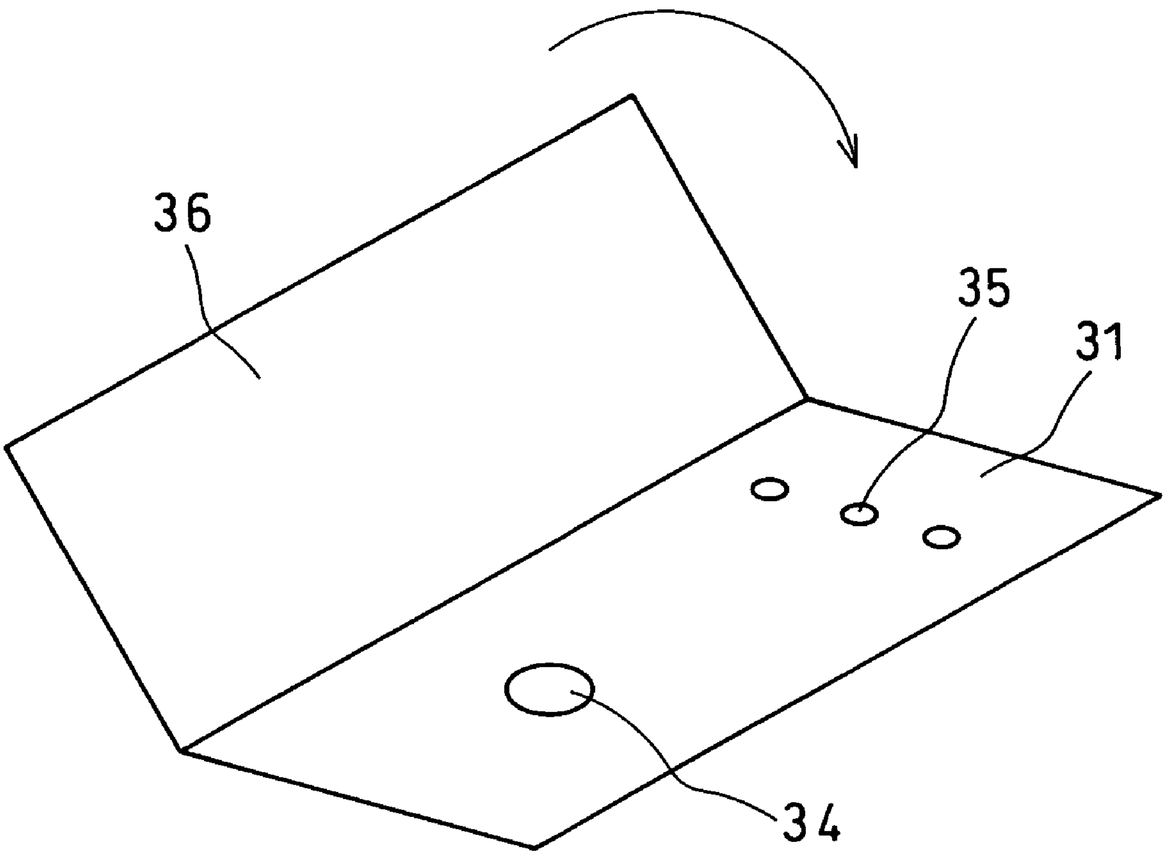
FIG. 4 is a perspective view illustrating the foregoing sample analysis device in a used state.

The sample analysis device of the third example principally is used for holding a sample or conserving a sample, and is particularly suitable for transporting a sample, for instance, by mail. For example, when whole blood is dripped through the sample supply hole 34 so as to be supplied to the porous sheet 33, the whole blood is transferred through the inside of the porous sheet 33 due to the capillary phenomenon, and is separated into blood cells and blood plasma (blood serum) due to the chromatography effect, while the blood plasma and blood serum are spread. Then, the separating 363 is removed, and as shown in FIG. 4, the protective film 36 is laminated on a surface of the supporting film 31, and is bonded using the bonding layer 362, so that the sample supply hole 34 and the air vent holes 35 are sealed. By so doing, the whole blood that is held in the porous sheet 33 in a state in which blood cells are separated is prevented from being brought into contact with outside air, whereby the degradation thereof is prevented for long periods. Therefore, even in the case where an examination laboratory is in a remote location, the foregoing device may be enclosed in an envelope or the like and mailed thereto. When blood plasma and blood serum components are to be analyzed in an examination laboratory, the sample analysis device thus mailed is taken out of the envelope, the sample is extracted from appropriate portions of the porous sheet 33 in the manner described above, and is analyzed.

Embodiment B

The following will describe the second sample analysis device of the present invention. It should be noted that the present invention is not limited to these embodiments.

Embodiment B-1

Figure 6:
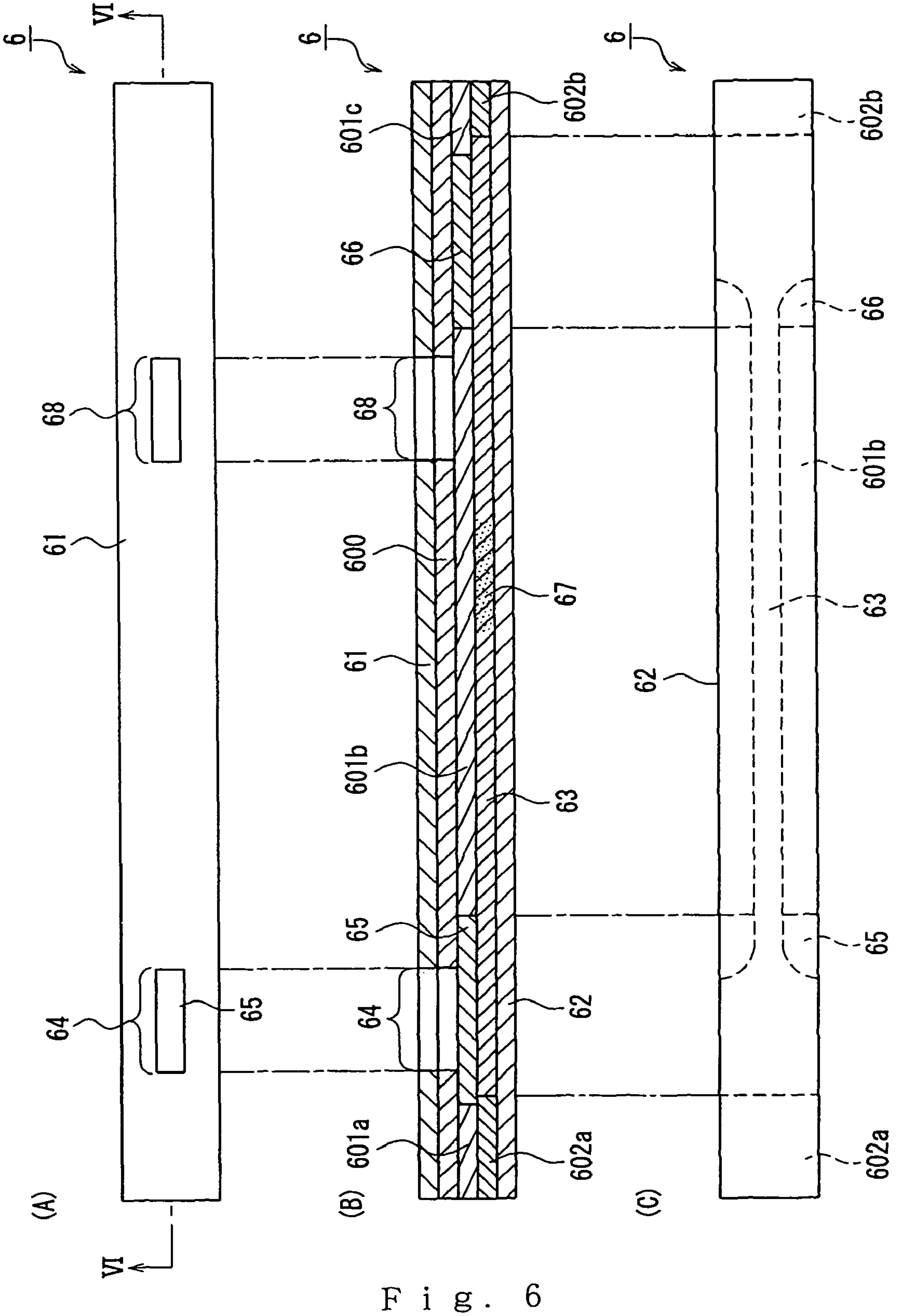
FIGS. 6A to 6C are views illustrating still another example of a sample analysis device of the present invention.

The following will describe an example of the second sample analysis device while referring to FIGS. 6A to 6C. FIG. 6A is a plan view of the sample analysis device. FIG. 6B is a cross-sectional view of the device along an arrow line VI-VI shown in the foregoing plan view of FIG. 6A, viewed in a direction indicated by the arrows. FIG. 6C is a bottom view of the device. Here, the left side of each drawing is referred to as an upstream side, while the right side thereof is referred to as a downstream side.

The sample analysis device 6 includes a cover film (supporting film) 61, a porous film 63, a base film 62, and bonding layers 600 to 602 (a first bonding layer 600, second bonding layers 601*a* to 601*c*, and third bonding layers 602*a* and 602*b*) for bonding the members with one another. On a surface of the base film 62, the porous film 63 is laminated in the vicinity of the center thereof, and the third bonding layers 602*a* and 602*b* are laminated at ends thereof in a lengthwise direction. The porous film 63 has a reagent-containing portion 67 that is impregnated with a reagent substantially at the center in a lengthwise direction of the porous film 63. Further, on a surface of the porous film 63, a separating layer 65 is laminated at an end thereof (on the left side in the drawings), and a water-absorbing layer (absorbing layer) 66 is laminated at the other end thereof (on the right side in the drawings). Between the separating layer 65 and the absorbing layer 66, the second bonding layer 601*b* having a thickness equal to that of the separating layer 65 and the absorbing layer 66 is bonded. Still further, on surfaces of the third bonding layers 602*a* and 602*b*, the second bonding layers 601*a* and 601*c* having a thickness equal to that of the separating layer 65 and the absorbing layer 66 are arranged. The first bonding layer 600 and the cover film 61 are laminated in the stated order on entire surfaces of the second bonding layers 601*a*, 601*b*, and 601*c*, the separating layer 65, and the absorbing layer 66, and this laminate of the cover film 61 and the first bonding layer 600 has two through holes that go through the both and that are arranged in the lengthwise direction thereof so as to be parallel with each other. Among these through holes, the one located on the upstream side constitutes a sample supply part 64, and the other located on the downstream side constitutes a detection part 68. The sample supply part 64 is located at a position corresponding to the separating layer 65, while the detection part 68 is located at a position between the reagent-containing portion 67 of the porous film 63 and the absorbing layer 66.

The size of the sample analysis device 6 may be determined appropriately according to the type of a sample to be analyzed or the amount of the same, and for instance, the sample analysis device has an overall length in a range of 10 mm to 200 mm, an overall width in a range of 10 mm to 200 mm, and a thickness in a range of 0.5 μm to 10 μm. It should be noted that the "length" indicates a length in the lengthwise direction of the sample analysis device 1, while the "width" indicates a length in a width direction (this also applies to the following).

For instance, the cover film 61 has a size in the following range: a length of 10 mm to 200 mm; a width of 10 mm to 200 mm; and a thickness of 0.05 mm to 8 mm. The sample supply part 64 has a size in the following range: a length of 1 mm to 50 mm; a width of 1 mm to 50 mm; and a thickness of 0.05 mm to 8 mm. The detection part 68 has a size in the following range: a length of 1 mm to 50 mm; a width of 1 mm to 50 mm; and a thickness of 0.05 mm to 8 mm. Further, the first bonding layer 600 preferably has, for instance, a length and a width equal to those of the cover film 61, respectively, which are a length of 10 mm to 200 mm and a width of 10 mm and 200 mm, and it preferably has a thickness of 0.05 mm to 8 mm, for example.

The separating layer 65 has a size, for instance, in the following range: a length of 1 mm to 100 mm; a width of 1 mm to 100 mm; and a thickness of 0.05 mm to 8 mm.

The absorbing layer 66 has a size, for instance, in the following range: a length of 1 mm to 100 mm; a width of 1 mm to 100 mm; and a thickness of 0.05 mm to 8 mm.

The second bonding layers 601*a* to 601*c* preferably has a thickness, for instance, equal to that of the blood cell separating layer 65 and the absorbing layer 66.

The porous sheet 63 has, for instance, a length of 10 mm to 200 mm, a width of 10 mm to 200 mm, and a thickness of 0.05 mm to 8 mm. The average diameter of pores of the porous sheet 63 is not limited particularly as long as it is in a range such that a sample is spread due to the capillary phenomenon. The average diameter of pores is, for instance, 0.02 μm to 100 μm, preferably 0.1 μm to 10 μm, more preferably 1 μm to 5 μm. Further, the third bonding layers 602*a* and 602*b* preferably have a thickness, for instance, equal to that of the porous sheet 63.

The following will describe a method for producing the sample analysis device 6, but the method is not limited to those described below.

First of all, the first bonding layer 600 is laminated on a bottom face of the cover film 61, and through holes that are to constitute the sample supply part 64 and the detection part 68 are provided through the laminate thus obtained. Alternatively, the cover film 61 and the first bonding layer 600 in which through holes are provided beforehand may be laminated.

The material for the cover film (supporting film) 61 is not limited particularly, and examples of the material include various types of resin sheets as described above. Among these, polyethylene terephthalate is particularly preferable, since it excels in cost and processibility as well as in handlability due to combination of its plasticity and elasticity as its properties. Such a plastic sheet may be produced by a known conventional method, or alternatively, a plastic sheet in a roll form or a sheet form available in the market may be used.

The first bonding layer 600 is not limited particularly, and, examples applicable as the same include sheet-form bonding materials and liquid-form or gel-form bonding materials such as a glue. Among these, a sheet-form bonding material is preferable since it is easy to handle, and a double-faced tape is particularly preferable. It should be noted that in the case where the liquid-form or gel-form bonding material is used, the material may be applied over a bottom face of the cover film 61 having through holes so as to have a uniform thickness. The thickness can be controlled by using, for instance, a roller or the like.

Next, on a bottom face of the first bonding layer 600, the separating layer 65 is bonded in a manner such that the separating layer covers the sample supply part 64, and the absorbing layer 66 is bonded on a downstream side with respect to the detection part 68.

The separating layer 65 may have, for instance, at least a function of removing unnecessary material in a sample, and examples of the material for the same include porous materials such as glass films, filter paper, resin-based porous sheets, etc. Examples of the resin usable in the resin-based porous sheets include polypropylene, polyethylene, polyvinylidene fluoride, ethylene-vinyl acetate, acrylonitrile, polytetrafluoroethylene, etc.

The average diameter of pores of the separating layer 65 can be determined appropriately according to, for instance, the type of the sample and the type of unnecessary matters. In the case where the sample is whole blood and blood cells are to be separated, the separating layer 65 may have an average pore diameter such that the blood cells do not pass through pores, and for instance, it is 1 μm to 500 μm, preferably 2 μm to 100 μm, more preferably 5 μm to 50 μm.

The absorbing layer 66 is not limited particularly as long as it absorbs a sample rapidly. Examples of the material for the same include moisture absorbing materials, porous materials, and fibrous materials, and more specifically, dry gels, filter paper, and porous plastics. Examples of the porous plastics include polypropylene, polyethylene, polyvinylidene fluoride, ethylene-vinyl acetate, acrylonitrile, polytetrafluoroethylene, etc. Further, such an absorbing layer preferably is treated with a surfactant beforehand so as to have hydrophilicity, since by so doing the hydrophobicity inherent to the material can be reduced. This makes it possible to further improve the water-absorbing property.

It should be noted that the absorbing layer 66 preferably is configured so that, in a finished sample analysis device, it has exposed side faces as shown in FIG. 6B, or it has an exposed portion on which the porous sheet 63 is not overlapped as shown in FIG. 6C. Such exposure allows for an air vent, thereby causing the sample to be spread smoothly. Further, this enables the observation of the exposed portion, thereby making it easier to check whether or not the sample is spread to the absorbing layer 66.

Subsequently, the second bonding layers 601*a*, 601*b*, and 601*c* are bonded at both ends of the bottom face of the first bonding layer 600 in the lengthwise direction and between the blood cell separating layer 65 and the absorbing layer 66. As the material for the second bonding layer, the same material as that for the first bonding layer can be used. Thus, by providing the second bonding layer 601*b* between the blood cell separating layer 65 and the absorbing layer 66 so as to fill a gap therebetween, the integrated configuration of the sample analysis device is not impaired even with, for instance, shocks during the preservation or transport, and a sample is prevented from entering a gap between the blood cell separating layer 65 and the absorbing layer 66.

On the other hand, the base film 62 is prepared, and the third bonding layers 602*a* and 602*b* are laminated at both ends of the base film 62 in the lengthwise direction, while the porous sheet 63 is arranged between the third bonding layers 602*a* and 602*b*.

A material for the base film 62 is not limited particularly, and for instance, the same material as that for the cover film 61 can be used. As a material for the third bonding layers, the same material as that for the first bonding layers can be used.

As the porous sheet 63, those described above can be used. Particularly, in the case where the porous sheet 63 is a symmetric porous sheet whose pore structure is substantially homogeneous, liquid impregnated in the sheet is spread radially. However, by increasing the length of the porous sheet, the spreading in the lengthwise direction is promoted, and by decreasing the width of the porous sheet, the spreading in the lengthwise direction further is promoted. Therefore, as shown in FIG. 6C, in the porous sheet, a portion thereof corresponding to the sample supply part 64 preferably has an increased area so as to sufficiently hold the sample, while a portion thereof where the sample is spread preferably has a decreased width.

Further, a portion of the porous sheet 63 is impregnated with a reagent as described above beforehand so that the reagent-containing portion 67 is formed before the porous sheet 63 is laminated on the base film 62. The reagent-containing portion 67 can be formed by, for instance, impregnating the porous sheet with a solution containing the reagent by printing, impregnation, spraying, or another method, and drying the same.

Still further, in the case where the porous sheet 63 is caused to contain reagents in a direction parallel with a direction in which a sample is spread, the sample can be analyzed regarding a multiplicity of items with use of one sample analysis device. In this case, boundary layers preferably are provided by, for instance, impregnating the sheet with a hydrophobic resin solution, so as to prevent the reagents for the multiple items from being mixed with one another.

Subsequently, the cover film 61 on which the separating layer 65 and the absorbing layer 66 are laminated, and the base film 62 on which the porous sheet 63 is laminated, are stacked on each other, whereby the first sample analysis device 6 is produced as shown in FIG. 6B.

The following will describe an example in which whole blood is a sample and a target component in blood serum is analyzed using this sample analysis device 6. First, when a whole blood sample is dripped on the sample supply part 64, the whole blood is separated into blood serum and blood cells by the separating layer 65. The blood serum having passed through the separating layer 65 reaches the porous sheet 63, and is spread to the downstream side due to the capillary phenomenon. The blood serum reaching the reagent-containing portion 67 dissolves the reagent, whereby a target component in the blood serum reacts with the reagent. A reaction product resulting from the reaction is spread further to the downstream side with the blood serum, thereby reaching the detection part 68. It should be noted that since the absorbing layer 66 is arranged at the downstream end of the porous sheet 63, blood serum thus spread is absorbed by the absorbing layer 66, whereby the spreading of the serum is accelerated. Finally, the reaction product spread to the detection part 68 can be detected from the detection part 68 by an electrochemical scheme or an optical scheme (including visual observation).

Since the sample analysis device 6 as described above is downsized easily, it is possible to reduce the necessary amount of a sample, for instance.

It should be noted that in the present embodiment, a through hole is provided in the cover film 61 so as to constitute a detection part, but the detection part is not limited to this configuration. For instance, an optically transparent member may be used as the cover film or the base film as well as the bonding layers, so that the measurement is carried out without a through hole. Examples of materials for such optically transparent members include polyethylene terephthalate (PET), polypropylene (PP), polyethylene (PE), and polystyrene (PS), among which PP is preferable.

Embodiment B-2

Figure 7:
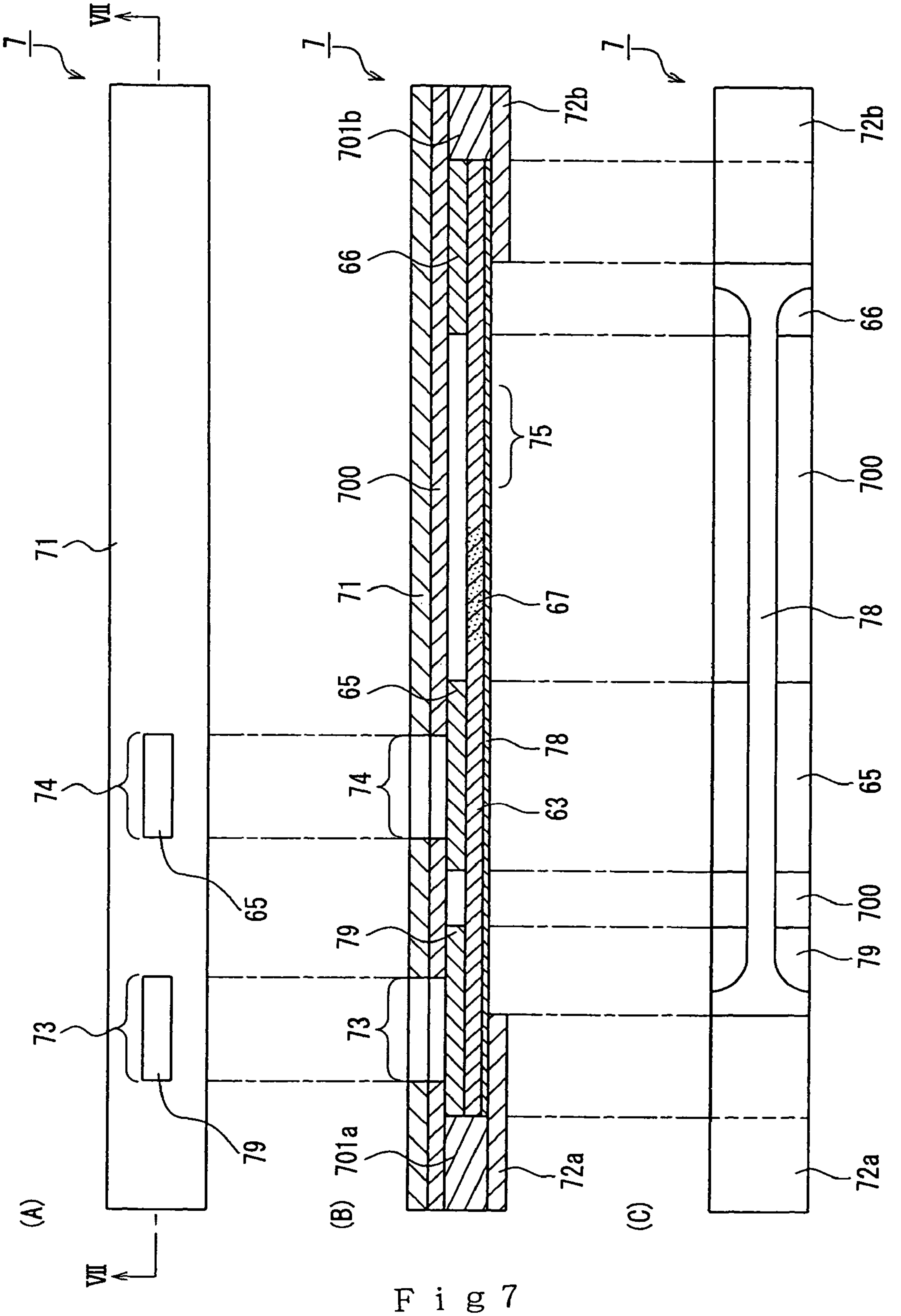
FIGS. 7A to 7C are views illustrating still another example of a sample analysis device of the present invention.
Figure 8:
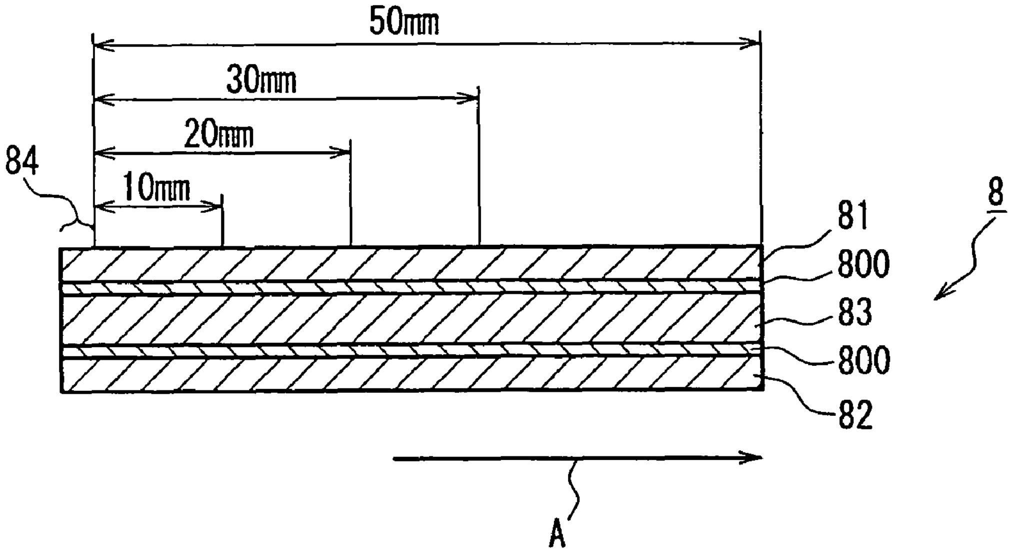
FIG. 8A is a cross-sectional view illustrating still another example of a sample analysis device of the present invention.
FIG. 8B is a cross-sectional view of a comparative example for the same.
Figure 8:
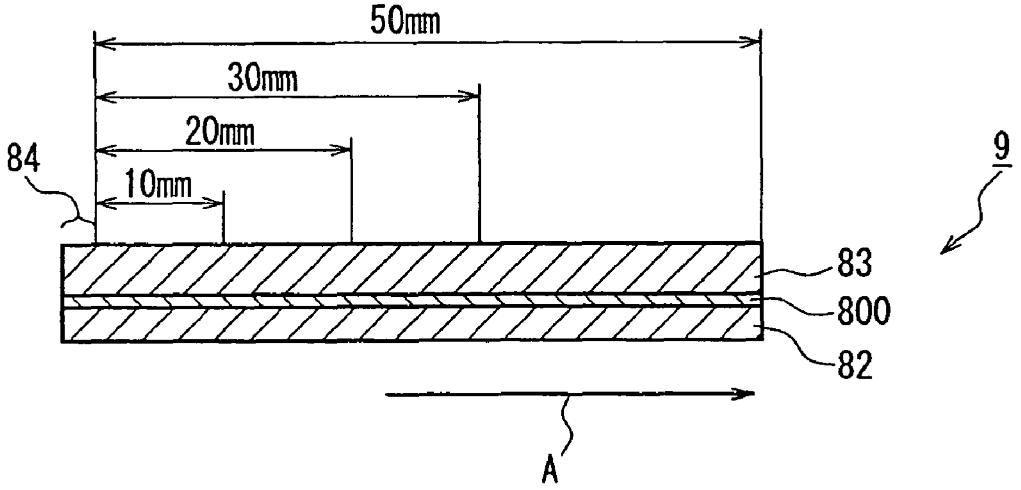

Another example of the second sample analysis device is described, with reference to FIGS. 7A to 7C. FIG. 7A is a plan view of the foregoing sample analysis device. FIG. 7B is a cross-sectional view of the device along an arrow line VII-VII shown in FIG. 7A, viewed in a direction indicated by the arrows. FIG. 7C is a bottom view of the device. It should be noted that the same members as those of Embodiment B-1 are designated with the same reference numerals.

The sample analysis device 7 includes a cover film 71, a porous sheet 63 having a reagent-containing portion 67, base films 72*a* and 72*b*, and bonding layers 700, 701*a*, and 701*b* for bonding the members with one another. On a bottom face of the porous film 63, a lining layer 78 is laminated integrally. On a top face of the porous film 63 on an upstream side with respect to the reagent-containing portion 67, a spreading solvent holding layer 79 and a separating layer 65 are arranged in the stated order from an end in a lengthwise direction with a space therebetween, while on the face thereof on a downstream side with respect to the reagent-containing portion 67, an absorbing layer 66 is arranged at the other end. The first bonding layer 700 and the cover film 71 that are longer in the lengthwise direction than the porous sheet 63 are laminated in the stated order on the spreading solvent holding layer 79, the separating layer 65, and the absorbing layer 66. The laminate of the cover film 71 and the first bonding layer 700 has two through holes that go through both of the cover film 71 and the first bonding layer 700 and that are arranged in the lengthwise direction so as to be parallel with each other. The through hole positioned on the upstream side constitutes a spreading solvent supply part 73, while the through hole positioned on the downstream side constitutes a sample supply part 74. The spreading solvent supply part 73 and the spreading solvent holding layer 79 are positioned so as to correspond to each other, and so are the sample supply part 74 and the separating layer 65. Further, on a bottom face of the first bonding layer 700, at both ends thereof, second bonding layer 701*a* and 701*b* are arranged, which function as adhesive and spacers. The second bonding layer 701*a*, as one of these, is adjacent to the lining layer 78, the porous film 63, and the spreading solvent holding layer 79, while the second bonding layer 701*b*, as the other one of these, is adjacent to the lining layer 78, the porous film 63, and the absorbing layer 66. On bottom faces of the second bonding layers 701*a* and 701*b*, base films 72*a* and 72*b* are arranged. The base films 72*a* and 72*b* have protrusions protruding toward the center in the lengthwise direction from the second bonding layers 701*a* and 701*b*, respectively. Therefore, the base films 72*a* and 72*b* are bonded partially with the second bonding layers 701*a* and 701*b*, respectively. On the protrusions of the base films 72*a* and 72*b*, a porous sheet 63 having the lining layer 78 is arranged, and the porous sheet 63 is caught between the spreading solvent holding layer 79 and the absorbing layer 66, which are fixed to the base films 72*a* and 72*b*, respectively, and to the cover film 71. In other words, this is a state in which the porous sheet is caught indirectly between the cover film 71 and the base films 72*a* and 72*b*.

The sizes of the sample analysis device 7 and constituent members thereof are identical to those of the sample analysis device 6 of Embodiment B-1 unless indicated specifically. The spreading solvent supply part 73 of the sample analysis device 7 has a size, for instance, in a range of 0.5 mm (length)×0.5 mm (width) to 50 mm (length)×50 mm (width), preferably in a range of 1 mm (length)×1 mm (width) to 30 mm (length)×30 mm (width), more preferably in a range of 3 mm (length)×3 mm (width) to 10 mm (length)×10 mm (width), particularly preferably in a range of 5 mm (length)×3 mm (width).

The spreading solvent holding layer 79 has a size of, for instance, in a range of 1 mm (length)×1 mm (width)×50 μm (thickness) to 100 mm (length)×100 mm (width)×8000 μm (thickness), preferably in a range of 2 mm (length)×2 mm (width)×100 μm (thickness) to 50 mm (length)×50 mm (width)×4000 μm (thickness), more preferably in a range of 4 mm (length)×4 mm (width)×200 μm (thickness) to 30 mm (length)×30 mm (width)×2000 μm (thickness).

The lining layer 78 has the same length and width as those of the porous sheet 63 preferably, and has a thickness of, for example, 20 μm to 4000 μm, preferably 40 μm to 2000 μm, more preferably 80 μm to 1000 μm.

Each of the base films 72*a* and 72*b* has a size of, for instance, in a range of 1 mm (length)×1 mm (width)×50 μm (thickness) to 100 mm (length)×100 mm (width)×8000 μm (thickness), preferably in a range of 2 mm (length)×2 mm (width)×100 μm (thickness) to 50 mm (length)×50 mm (width)×4000 μm (thickness), more preferably in a range of 4 mm (length)×4 mm (width)×200 μm (thickness) to 30 mm (length)×30 mm (width)×2000 μm (thickness).

Each of the second bonding layers 701*a* and 701*b* has a size of, for instance, in a range of 1 mm in length×1 mm in width×50 μm in thickness to 100 mm in length×100 mm in width×8000 μm in thickness, preferably in a range of 2 mm in length×2 mm in width×100 μm in thickness to 50 mm in length×50 mm in width×4000 μm in thickness, more preferably 4 mm in length×4 mm in width×200 μm in thickness.

The sizes of the spreading solvent holding layer 79, the separating film 65, and the absorbing layer 66 are not limited particularly, but they preferably have the same thickness since this facilitates the production of the sample analysis device.

The following will describe a method for producing the foregoing sample analysis device, but the method is not limited to these examples described below. It should be noted that the sample analysis device is produced in the same manner as that of Embodiment B-1 described above unless indicated specifically.

First of all, the cover film 71 and the first bonding layer 700 are laminated, and through holes that are to constitute the spreading solvent supply part 73 and the sample supply part 74 are provided.

Next, the separating layer 65 and the water absorbent layer 66 are bonded on a bottom face of the first bonding layer 700, and further, the spreading solvent holding layer 79 is bonded thereon so as to cover the spreading solvent supply part 73.

The spreading solvent holding layer 79 is not limited particularly as long as it is capable of absorbing and holding a spreading solvent and supplying the spreading solvent to the porous sheet. Examples of the material for the same include filter paper, cellulose sheets, porous sheets made of resin, and glass filters. More specifically, a porous sheet made of nitrocellulose, a porous sheet made of polyester, a porous sheet made of polysulfone, or the like can be used.

On the other hand, the base films 72*a* and 72*b* are prepared, and the second bonding layers 701*a* and 701*b* are laminated on ends in a lengthwise direction of surfaces of the base films 72*a* and 72*b*, respectively.

The material for the base films 72*a* and 72*b* is not limited particularly, and, for instance, the same materials as those for the base film in Embodiment B-1 can be used, among which PET, PE, and PS are preferable.

The material for the second bonding layers 701*a* and 701*b* is not limited particularly, and the same materials for the bonding layers in Embodiment B-1 can be used. The second bonding layers not only function for bonding the base films 72*a* and 72*b* with the cover film 71, but also function as spacers for securing a space in the sample analysis device 7 in which the spreading solvent holding layer 79, the separating layer 65, the absorbing layer 66, and the porous film 63 having the lining layer 78 are arranged. It should be noted that each of the second bonding layers 701*a* and 701*b* may be composed of a single layer, or alternatively, it may be composed of a laminate formed by, for instance, laminating sheet-form bonding materials, since in this case the thickness can be adjusted appropriately.

Subsequently, the base films 72*a* and 72*b* are arranged so as to be positioned at both ends of the sample analysis device, respectively, and ends of the porous sheet 63 having the lining layer 78 are arranged on the protrusions of the base films 72*a* and 72*b*, respectively, on which the second bonding layers 701*a* and 701*b* are not laminated.

The lining layer 78 of the porous sheet 63 is not limited particularly, and a plastic film generally used can be used as the lining layer 78. More specifically, examples of the lining layer 78 include films made of nylon resin, polyester resin, cellulose acetate, PE resin, PET, PP resin, polyvinyl chloride, acrylic resin, etc. In addition to these, synthetic rubber and the like can be used. Among these, PE, PET, PP, and polyvinyl chloride (PVC) are preferable, and polyethylene terephthalate is particularly preferable, since it excels in cost and processibility as well as in handlability due to its plasticity and elasticity in combination as its properties. Such a plastic film may be produced by a known conventional method, or alternatively, a plastic sheet in a roll form or a sheet form available in the market may be used. It should be noted that since the detection part 75 according to Embodiment B-2 is positioned on the lining layer side, the lining layer 78 preferably is optically transparent, and examples used as the optically transparent plastic film include films made of PP, PET, etc.

Further, a porous thin film may be formed on a surface of the lining layer 78 so as to produce the porous sheet 63 provided integrally with the lining layer 78, or alternatively, for instance, the lining layer 78 and the porous sheet 63 that are prepared separately may be brought into close contact with each other using an adhesive or the like. Alternatively, a commercial product in which the lining layer 78 and the porous sheet 63 are provided integrally may be used. More specifically, a commercial product obtained by laminating a film made of PET or PVC as a lining layer on a nitrocellulose film, a porous sheet made of PE, or the like can be used.

In the case where the porous sheet 63 thus has the lining layer 78, a sufficient strength can be achieved even if the base film is not arranged over an entirety of a bottom face of a porous sheet as is the case with Embodiment B-1.

Then, by bonding the base films 72*a* and 72*b* with the cover film 71 via the second bonding layers 701*a* and 701*b*, respectively, the second sample analysis device 7 is produced. It should be noted that in the sample analysis device 7, a region 75 of the porous sheet between the reagent-containing part 67 and the absorbing layer 66 on the side of the lining layer 78 constitutes the detection part.

The sample analysis device 7 is configured so that the porous sheet 63 itself is bonded neither to the base films 72*a* and 72 nor to the cover film 71, but is caught between the protrusion of the base film 72*a* and the spreading solvent holding layer 79 bonded with the cover film 71, as well as between the protrusion of the base film 72*b* and the absorbing layer 66 bonded with the cover film 71, so that the porous sheet 63 is fixed therein. This makes it possible to maintain the sample analysis device 7 in an integrated configuration as a whole.

The following will describe an example of a sample analysis operation in which the foregoing sample analysis device 7 is used, whole blood is a sample, and a target component in the whole blood is analyzed. First, when a whole blood sample is dripped to the sample supply part 74, the whole blood is separated into blood serum and blood cells by the separating layer 65. The blood serum having passed through the separating layer 65 reaches the porous sheet 63, and is spread toward the downstream side due to the capillary phenomenon. On the other hand, a spreading solvent such as water or a buffer solution is dripped to the spreading solvent supply part 73, the spreading solvent first is absorbed and held by the spreading solvent holding layer 79, and then, infiltrates into the porous sheet 63 via a contact face therebetween. The spreading solvent having infiltrated into the porous sheet 63 is spread in the lengthwise direction due to the capillary phenomenon, thereby aiding in spreading the blood serum while being spread together. Finally, the target component in the blood serum and the reagent in the reagent-containing part 67 react with each other, and a reaction product obtained is detected by the detection part 75.

EXAMPLES

Sample analysis devices in each of which supporting films were stuck on both sides of a porous sheet were produced, and influences of environmental (humidity and temperature) changes on the time over which a sample is spread (spreading time) were examined.

A nitrocellulose film with a thickness of 150±10 μm, an average pore diameter of 10 μm, a length of 50 mm, and a width of 7 mm was prepared as the porous sheet, while PET films, each of which had the same size as that of the porous sheet and a thickness of 50 μm, were prepared as supporting films. The supporting films were stuck on both sides of the porous sheet using double-faced tapes, each of which had the same size as that for the porous sheet (thickness: 100 μm, trade name: HJ-3160W, produced by NITTO DENKO CORPORATION). Thus, a sample analysis device that was used as the example of the present invention was produced.

On the other hand, as the comparative example, a sample analysis device was produced by using the same materials as those for Example as described above, and sticking a supporting film only on a rear face of the porous sheet using a double-faced tape.

The sample analysis devices of the example and the comparative example were subjected to the following test: under conditions of constant temperature (22° C.) and varied humidity (RH 35%, RH 50%), 40 μL of a 1-wt % solution of a blue-color coloring agent (Blue No.2) was spotted in an area of 3 mm from an end of the device in the lengthwise direction, and respective times that it took for the blue-color coloring agent solution to spread to positions of 10 mm, 20 mm, and 30 mm from the spotted portion were measured. It should be noted that the measurement was carried out using three sample analysis devices of the example and three of the comparative example for each condition. Regarding each device, a time per a distance of 10 mm from the position of 10 mm to the position of 20 mm, and a time per a distance of 10 mm from the position of 20 mm to the position of 30 mm were calculated. The results regarding the example (devices 1*a* to 1*f*) are shown in Table 1 below, while the results regarding the comparative example (devices 1*a* to 1*f*) are shown in Table 2 below. It should be noted that in Tables 1 and 2, averages of the measurement results as to each condition are indicated in brackets.

TABLE 1

| | | Spreading Time to Position (sec.) | | | Spreading Time per 10 mm (sec.) | |
|---|---|---|---|---|---|---|
| | | 10 mm | 20 mm | 30 mm | 10-20 mm | 20-30 mm |
| (RH 35%) | 1a | 17 | 63 | 137 | 46 | 74 |
| EXAMPLE | 1b | 18 | 65 | 139 | 47 | 74 |
| | 1c | 18 | 68 | 142 | 50 | 74 |
| | | | | | (47.7) | (74.0) |
| (RH 50%) | 1d | 19 | 67 | 142 | 48 | 75 |
| EXAMPLE | 1e | 16 | 64 | 137 | 48 | 73 |
| | 1f | 19 | 69 | 143 | 50 | 74 |
| | | | | | (48.7) | (74.0) |

TABLE 2

| | | Spreading Time to Position (sec.) | | | Spreading Time per 10 mm (sec.) | |
|---|---|---|---|---|---|---|
| | | 10 mm | 20 mm | 30 mm | 10-20 mm | 20-30 mm |
| (RH 35%) | 1a | 5 | 37 | 115 | 32 | 78 |
| COMPARATIVE | 1b | 4 | 38 | 116 | 34 | 78 |
| EXAMPLE | 1c | 5 | 41 | 119 | 36 | 78 |
| | | | | | (34.0) | (74.0) |
| (RH 50%) | 1d | 5 | 35 | 103 | 30 | 68 |
| COMPARATIVE | 1e | 4 | 30 | 100 | 26 | 70 |
| EXAMPLE | 1f | 5 | 31 | 95 | 27 | 64 |
| | | | | | (27.7) | (67.3) |

As shown in Table 2, in the case of the sample analysis device of the comparative example, the spreading time through the distance from the position of 10 mm to the position of 20 mm (spreading time through 10-20 mm) under humidity of RH 35% was 34.0 seconds on average, and a spreading time through 20-30 mm was 74.0 seconds on average. On the other hand, with the variation of humidity to RH 50%, the spreading time through 10-20 mm became 27.7 seconds on average, and the spreading time through 20-30 mm became 67.3 seconds on average. Thus, the variation of humidity causes a difference of approximately 6 to 7 seconds in each. In contrast, in the case of the sample analysis device of the example in which supporting films are stuck on both of surfaces of a porous sheet, the variation of humidity from RH 35% to RH 50% merely caused a difference of only approximately one second in the average spreading time through 10-20 mm, and further, regarding the average spreading time through 20-30 mm, the same results were obtained. Consequently, in the case of the sample analysis device of the example of the present invention, since the spreading time is not influenced by conditions such as humidity, it also is possible to suppress differences among sample analysis devices as to the time of reaction between a sample and a reagent, and measurement results with high reproducibility can be obtained.

INDUSTRIAL APPLICABILITY

As described above, the sample analysis device of the present invention has a simple configuration, and therefore, it is easy to produce and to downsize. Accordingly, it is particularly suitable for transporting a sample by mail or the like in a remote diagnosis system as described above. Further, since the sample analysis device of the present invention has excellent flexibility and operability, it allows testing to be carried out efficiently.

The invention claimed is:

1. A sample analysis device comprising:

a single layer porous sheet in which a sample is to be held;

a front face supporting film stuck on a front face of the single layer porous sheet, the front face supporting film having a sample supply hole in a part thereof, and an air vent hole at a position above the porous sheet, so that the front face supporting film is in contact with and extends beyond all peripheral portions of the front face of the single layer porous sheet; and a rear face supporting film stuck on a rear face of the single layer porous sheet so that the rear face supporting film is in contact with and extends beyond all peripheral portions of the rear face of the single layer porous sheet, wherein, the front face supporting film and the rear face supporting film are stuck on the single layer porous sheet so that capillary action of the sample between the supporting films and the single layer porous sheet does not occur as the sample spreads through the porous sheet when the device is being used, the front face supporting film and the rear face supporting film are bonded with each other around all peripheral portions of the single layer porous sheet so that all faces of the single layer porous sheet are sealed, and such that the front face supporting film is in contact with an entire surface area of the front face of the single layer porous sheet except at the sample supply hole and the air vent hole, and the rear face supporting film is in contact with an entire surface area of the rear face of the single layer porous sheet, the single layer porous sheet is a single layer asymmetric porous sheet in which diameters of pores vary in a thickness direction of the sheet, and the single layer asymmetric porous sheet has a groove parallel with a width direction of the sheet.

2. The sample analysis device according to claim 1, further comprising:

a protective film stuck on the front face supporting film having the sample supply hole.

3. The sample analysis device according to claim 1, wherein the asymmetric porous sheet has a reagent section containing a reagent, and has the groove parallel with a width direction of the sheet at a position between the sample supply hole and the reagent section.

4. The sample analysis device according to claim 1 wherein the porous sheet has a lining layer on its rear face.

5. The sample analysis device according to claim 4 further comprising:

at least one of a separating layer and a sample holding layer, arranged between the front face supporting film and the porous sheet at a position corresponding to the sample supply hole, the separating layer being for separating and removing unnecessary matters in the sample, and the sample holding layer being for temporarily holding the sample.

6. The sample analysis device according to claim 5, wherein the separating layer is bonded with the front face supporting film using a bonding member.

7. The sample analysis device according to claim 1 wherein the front face supporting film further includes a through hole that constitutes a spreading solvent supply hole on an upstream side with respect to the sample supply hole in a direction in which the sample is spread in the porous sheet.

8. The sample analysis device according to claim 7, further comprising:

a spreading solvent holding layer for holding a spreading solvent and supplying the same to the porous sheet, the spreading solvent holding layer being arranged between the front face supporting film and the porous sheet at a position corresponding to the spreading solvent supply hole.

9. The sample analysis device according to claim 8, wherein the spreading solvent holding layer is bonded on the front face supporting film using a bonding member.

10. The sample analysis device according to claim 1 further comprising:

an absorbing layer arranged between the front face supporting film and the porous sheet at an end on a downstream side in a direction in which the sample is spread in the porous sheet.

11. The sample analysis device according to claim 10, wherein the absorbing layer is bonded with the front face supporting film using a bonding member.

12. The sample analysis device according to claim 4 wherein at least one of the front face supporting film and the rear face supporting film includes a detection part on a downstream side with respect to the sample supply hole in a direction in which the sample is spread in the porous sheet.

13. The sample analysis device according to claim 12, wherein the detection part in the at least one of the front face supporting and the rear face supporting film is optically transparent.

14. The sample analysis device according to claim 12, wherein the detection part is a through hole provided in the at least one of the front face supporting film and the rear face supporting film.

15. The sample analysis device according to claim 1 wherein the porous sheet includes a reagent part containing a reagent on a downstream side with respect to the sample supply hole in a direction in which the sample is spread in the porous sheet.

16. The sample analysis device according to claim 15 wherein the porous sheet includes a reagent part containing a reagent between the sample supply hole and the detection part in a direction in which the sample is spread in the porous sheet.

17. The sample analysis device according to claim 12 or 13, wherein at least a part of the lining layer corresponding to the detection part is optically transparent.

18. The sample analysis device according to claim 11 wherein the bonding member is a double-faced tape.

19. The sample analysis device according to claim 1, wherein the sample analysis device is not enclosed in a housing.

* * * * *